United States Patent
Quinn

(10) Patent No.: US 6,846,876 B1
(45) Date of Patent: Jan. 25, 2005

(54) LOW ODOR, LIGHT COLOR, DISPOSABLE ARTICLE CONSTRUCTION ADHESIVE

(75) Inventor: Thomas H. Quinn, St. Paul, MN (US)

(73) Assignee: Adherent Laboratories, Inc., Woodbury, MN (US)

( * ) Notice: Subject to any disclaimer, the term of this patent is extended or adjusted under 35 U.S.C. 154(b) by 0 days.

(21) Appl. No.: 10/673,385

(22) Filed: Sep. 25, 2003

Related U.S. Application Data

(60) Provisional application No. 60/487,690, filed on Jul. 16, 2003.

(51) Int. Cl.$^7$ .............................................. C08F 210/02
(52) U.S. Cl. ........................ 524/570; 524/274; 524/579; 524/515; 524/71; 428/355; 428/219; 156/320; 156/325
(58) Field of Search ................................ 524/570, 274, 524/579, 515, 71; 428/355, 219; 156/320, 325

(56) References Cited

U.S. PATENT DOCUMENTS

| | | | |
|---|---|---|---|
| 3,181,765 A | 5/1965 | Bonzagni et al. | |
| 3,573,125 A | 3/1971 | Elliott | |
| 3,965,062 A | 6/1976 | Stiles | |
| 4,028,292 A | 6/1977 | Korpman | |
| 4,136,699 A | 1/1979 | Collins et al. | |
| 4,140,733 A | 2/1979 | Meyer, Jr. et al. | |
| 4,416,749 A | 11/1983 | Mahr et al. | |
| 4,460,364 A | 7/1984 | Chen et al. | |
| 4,497,941 A | 2/1985 | Aliani et al. | |
| 4,501,779 A | 2/1985 | Hsu et al. | |
| 4,526,577 A | 7/1985 | Schmidt, Jr. et al. | |
| 4,541,983 A | 9/1985 | Hsu et al. | |
| 4,587,289 A | 5/1986 | Comert et al. | |
| 4,590,106 A | 5/1986 | Hsu et al. | |
| 4,627,847 A | 12/1986 | Puletti et al. | |
| 4,671,987 A | 6/1987 | Knott et al. | |
| 4,745,026 A | 5/1988 | Tsukahara et al. | |
| 4,792,488 A | 12/1988 | Schirmer | |
| 4,880,696 A | 11/1989 | Yanidis | |
| 4,902,553 A | 2/1990 | Hwang et al. | |
| 4,909,390 A | 3/1990 | Raine et al. | |
| 4,929,509 A | 5/1990 | Godfrey | |
| 4,935,089 A | 6/1990 | Schirmer | |
| 4,935,271 A | 6/1990 | Schirmer | |
| 4,956,207 A | 9/1990 | Kauffman et al. | |
| 4,963,427 A | 10/1990 | Botto et al. | |
| 4,983,652 A | 1/1991 | Agarwal | |
| 5,061,262 A | 10/1991 | Chen et al. | |
| 5,064,492 A | 11/1991 | Friesch | |
| 5,066,694 A | 11/1991 | Agarwal et al. | |
| 5,075,143 A | 12/1991 | Bekele | |
| 5,120,787 A | 6/1992 | Drasner | |
| 5,149,741 A | 9/1992 | Alper et al. | |
| 5,183,706 A | 2/1993 | Bekele | |
| 5,331,033 A | 7/1994 | Stauffer et al. | |
| 5,352,717 A | 10/1994 | Bergishagen | |
| 5,411,786 A | 5/1995 | Kuo | |
| 5,454,909 A | 10/1995 | Morganelli | |
| 5,500,472 A | 3/1996 | Liedermooy et al. | |
| 5,605,720 A | 2/1997 | Allen et al. | |
| 5,620,758 A | 4/1997 | Babrowicz | |
| 5,670,566 A | 9/1997 | Liedermooy et al. | |
| 5,685,758 A | 11/1997 | Paul et al. | |
| 5,738,669 A | 4/1998 | Suzuki et al. | |
| 5,738,930 A | 4/1998 | Huskey | |
| 5,786,418 A | 7/1998 | Strelow et al. | |
| 5,843,260 A | 12/1998 | Huskey | |
| 5,853,864 A | 12/1998 | Bunnelle | |
| 5,928,782 A | 7/1999 | Albrecht | |
| 5,981,035 A | 11/1999 | Eshleman | |
| 6,024,822 A | 2/2000 | Alper et al. | |
| 6,107,430 A | * 8/2000 | Dubois et al. | ............ 526/348.5 |
| 6,117,945 A | 9/2000 | Mehaffy et al. | |
| 6,120,887 A | 9/2000 | Werenicz et al. | |
| 6,120,899 A | 9/2000 | Cameron et al. | |
| 6,184,285 B1 | 2/2001 | Hatfield et al. | |
| 6,288,149 B1 | 9/2001 | Kroll | |
| 6,300,398 B1 | 10/2001 | Jialanella et al. | |
| 6,319,979 B1 | 11/2001 | Dubois et al. | |
| 6,387,471 B1 | 5/2002 | Taylor et al. | |
| 6,406,767 B1 | 6/2002 | Mueller | |
| 6,430,898 B1 | 8/2002 | Remmers et al. | |
| 6,443,936 B1 | 9/2002 | Hamilton et al. | |
| 6,491,776 B2 | 12/2002 | Alper et al. | |
| 6,506,185 B1 | 1/2003 | Sauer et al. | |
| 6,534,572 B1 | 3/2003 | Ahmed et al. | |
| 6,547,915 B2 | 4/2003 | Taylor et al. | |
| 6,582,829 B1 | 6/2003 | Quinn et al. | |
| 2003/0139516 A1 | 7/2003 | Quinn et al. | |

OTHER PUBLICATIONS

KRATON™ Material Safety Data Sheet, 7 pages.
SEPTON™ Product Data Sheet, 13 pages.

* cited by examiner

Primary Examiner—David W. Wu
Assistant Examiner—Satya Sastri
(74) Attorney, Agent, or Firm—Merchant & Gould P.C.

(57) ABSTRACT

We have found a novel spray-on adhesive composition made from components including a high melt index polymer and a high melt tackifier that interact to produce a composition that can form a low odor, light color, non-tacky, hot melt adhesive material that can be used in disposable article manufacture. The adhesive is thermally stable at hot melt application conditions, is low in cost, is easily applied and produces high quality disposable articles.

14 Claims, No Drawings

LOW ODOR, LIGHT COLOR, DISPOSABLE ARTICLE CONSTRUCTION ADHESIVE

RELATED APPLICATION

This application claims priority under 35 U.S.C. §119(e) to U.S. provisional application Ser. No. 60/487,690 filed on Jul. 16, 2003, incorporated by reference herein.

FIELD OF THE INVENTION

The invention relates to an adhesive and to a composite article made by joining components with the adhesive. In one embodiment, a disposable article can be made by adhesively bonding layers including a film, a woven or non-woven fabric, tissue or sheet to a sheet-like material using a novel hot melt adhesive that can be variously applied or can be sprayed. Still further, the invention relates to the manufacture of a disposable composite article having a cover and an absorbent layer, held within the cover. The cover can be formed from a porous sheet adhered to a fluid impervious backing layer and can have further fabrics, sheets or films added. The absorbent layer can be made of a tissue, an absorbent, or combinations of an absorbent and outer cover layers. The adhesive of the invention is used to bind the components in a mechanically stable article or to join the outer cover to the absorbent. The sprayable hot melt adhesive composition typically contains a novel blend of thermoplastic copolymer and a compatible tackifying resin. Disposable articles such as an infant or adult diaper and feminine pads can be made with this adhesive material.

BACKGROUND OF THE INVENTION

Disposable articles and their construction materials including fabrics, films, and adhesives are described in a variety of United States patents. In initial work, Korpman, U.S. Pat. No. 4,028,292, teaches a heat resistant adhesive material comprising a reactive phenol formaldehyde resin and a suitable antioxidant of a metal dithiocarbamate. Collins et al., U.S. Pat. No. 4,136,699, teach a disposable article using a hot melt ABA block polymer containing pressure sensitive adhesive as a positioning and construction material. Similarly, Chen et al., U.S. Pat. No. 4,460,364, teach a hot melt PSA used in the disposables. Schmidt, Jr. et al., U.S. Pat. No. 4,526,577, teach SBS block copolymers system in disposables using multiline application technology. Puletti et al., U.S. Pat. No. 4,627,847, also teach the use of hot melts in disposables. Tsukahara, U.S. Pat. No. 4,745,026, teaches a delayed tack sheet using an aqueous dispersion of, e.g., a polymer, a solid plasticizer and preferably a tackifier. Quinn et al., U.S. Patent Publication No. US 2003/0139516 A1 teach certain hot melt adhesives utilizing a very broad range of materials. Quinn et al., U.S. Pat. No. 6,582,829 teach certain hot melt adhesives utilizing an ethylene α-olefin (EAO) polymer. The application discloses a very broad range of materials. Dubois et al, U.S. Pat. No. 6,107,430 teach a broad range of proposed formulations and teaches a 1000 melt index ethylene octene polymer (one type of EAO) combined with a tackifying resin, a wax and an antioxidant material. Werenicz et al., U.S. Pat. No. 6,120,887 teach hot melt adhesive compositions using, on the whole, exemplary materials generally containing less than 40% of a low MI (high molecular weight) polymer material. Jialanella et al., U.S. Pat. No. 6,300,398 relates to an ethylene □-olefin polymer mixture with a wax and a nucleating agent to improve elongation at break of the polymer material. While the disclosure mentions the use of these materials in adhesives, no specific formulatory strategies are shown in the reference. Polymer compositions in the form of mixtures of materials are shown in the patent from Column 20, line 50 through Column 24, line 27. Dubois et al., U.S. Pat. No. 6,319,979 teach low application temperature hot melt adhesives including an ethylene α-olefin polymer material. The patent has a very broad disclosure, but discloses exemplary materials beginning at Column 25, line 62 through Column 30, line 36. As a whole, the materials have less than 33% of the ethylene octene polymer (having a 1000 gm–10 min$^{-1}$ melt index). In Table III in Column 28 further shows additional examples using certain polymeric materials with a melt index (MI) of 500 or 1000 gr–10 min$^{-1}$ and in amounts less than 33 wt-%. Ahmed et al., U.S. Pat. No. 6,534,572 show compositions comprising a thermoplastic component and a superabsorbent polymer material. Kroll et al., U.S. Pat. No. 6,579,915 teach certain radiation crosslinked or curable hot melt adhesives utilizing low application temperatures. The application discloses a very broad range of materials, but uses a vinyl modified block polymer a KX-222CS. The vinyl substituent on the block polymer is used for radiation cross-linking.

The adhesive compositions of the invention are useful for a variety of disposable construction applications. The adhesive is low in odor. Low odor compositions substantially improve the working environment of workers who maintain equipment used in spraying the adhesive onto the workpiece. Further, the disposable articles, when removed from their packaging also have little or no detectable odor which can be unacceptable to many end users. The adhesive of the invention is also light in color, resulting in a clear, substantially transparent glue line on the disposable materials. Typical disposables are made from white or transparent, woven or non-woven fabrics, polyethylene or polyester films and colored or charred adhesives are unacceptable in such construction applications. The adhesive of the invention is preferably not tacky, preferably pelletizable. Pelletizable adhesives are relatively easy to package and use at the disposable assembly location. The adhesive is thermally stable such that it can be placed into applications equipment and be maintained for a substantial period of time at hot melt temperature prior to application.

A substantial need exists in this art to obtain such a low odor, light color, non-tacky, non-pressure sensitive (pelletizable), thermally stable, hot melt adhesive. Lastly, the adhesive material of this invention is formulated to minimize cost, and maximize adhesive performance without any reduction in quality in the resulting disposable article.

BRIEF DISCUSSION OF THE INVENTION

We have found an improved hot melt non-pressure sensitive adhesive. The material can be used as a novel spray-on adhesive composition made from a high MI polymer and a high melt tackifier component that interacts to produce a composition that can form a low odor, light color, non-tacky, hot melt adhesive material that can be used in disposable article manufacture. The adhesive is thermally stable at hot melt application conditions, is low in cost, is easily applied and produces high quality disposable articles.

A first embodiment of the invention is a hot melt, preferably non-pressure sensitive, adhesive composition. A second embodiment of the invention is a disposable article using the hot melt adhesive in a construction application. A third embodiment of the invention is a method using the hot melt of the invention to assemble a disposable article.

The adhesive can comprise, in its entirety, one of a number of useful polymers, a blend of polymers, or alternatively the adhesive can comprise a hot melt adhesive comprising at least one polymer admixed with other thermoplastic diluents such as tackifying resins, etc. The polymer provides the properties such as cohesiveness and strength. The polymer is typically combined with a tackifier or other material to modify the adhesive properties for use in the intended application. The blend of materials is formulated to exhibit the same desired properties. In this material relatively high melt or high viscosity tackifier is combined with relatively low molecular weight (high MI) thermoplastic components to enhance the cohesive strength of the mixture while maintaining good processability.

In production of disposables, a hot melt adhesive (HMA) is typically extruded at elevated temperature onto the disposable. Layers of a fabric or film can be added and blended. Disposables with secure bonding that traps layers of fabric or tissue in the HMA can be made because the adhesive can be extruded directly on the work piece. In recent years, increasing attention has been directed to development of sprayable hot melt adhesives. The work piece or substrate-manufacturing regimen can use a spray-on adhesive to increase productivity. Such spray-on adhesives are delivered from a plurality of narrow orifices in the form of fibers, threads or filaments having a substantially circular cross-section with a diameter less than 0.05 inch, typically about 0.01 to 0.001 inch. Fine line or spiral spray patterns are used. The spray-on adhesive takes on the form of fibers that have substantial surface area in comparison to the mass of the fiber. Typically, after spraying, the adhesives reach ambient temperatures upon immediate contact with the work piece. Extruded hot melt adhesives retain a significant amount of heat after application. Ambient temperature is the temperature of the surrounding environment and temperature of the disposable. In these construction applications, the disposable and the temperature of the environment are typically not substantially different. Sprayed adhesives take the form of a solid matrix formed as a result of the combined application adhesive fibers creating an overlapping distribution of threads or fibers on the disposable. Spray adhesive technology is used to make disposable articles by combining, e.g. a film with a woven or non-woven fabric with the adhesive and forming a bond between the substrates or layers by pressure. Such conventional spray-on adhesives form typically a laminated adhesive bonding with the film sheet and the fabric layers.

DETAILED DESCRIPTION OF THE INVENTION

Accordingly, a wide variety of thermoplastic polymers are suitable for use in the invention. Such thermoplastic polymers are preferably water insensitive. The term "polymer" is used herein to indicate a copolymer, terpolymer, or higher order polymer, a vinyl polymer, an ethylene-based polymer, a block polymer or other polymer with a molecular weight and melt characteristics that can provide useful adhesive properties. At least one other comonomer can be polymerized with ethylene to make the polymer. Polymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, octene, hexene, and mixtures thereof. Polymers of ethylene such as ethylene-vinyl-acetate (EVA), ethylene-methyl acrylate (EMA) and ethylene n-butyl acrylate (EnBa); ethylene carbon dioxide, and mixtures thereof can be used.

Suitable ethylene/unsaturated carboxylic acid, salt and ester polymers include ethylene/vinyl acetate (EVA) ethylene/acrylic acid (EEA) and its ionomers; ethylene/methacrylic acid and its ionomers; ethylene/methyl acrylate (EMA); ethylene/ethyl acrylate; ethylene/n-butyl acrylate (EnBA); as well as various derivatives thereof that incorporate two or more comonomers.

A thermoplastic hot melt adhesive composition comprising a thermoplastic ethylene based polymer containing at least one comonomer. Examples include ethylene acrylic materials, ethylene vinyl acetate (EVA) materials and others. Such adhesives can be prepared in combination with an appropriate high petroleum based tackifying material having a defined thermal aspect. The thermoplastic, typically non-tacky adhesive composition comprises a thermoplastic polymer. The polymer has a melt index grater than about 1000 grams–10 min$^{-1}$, often greater than 2000 grams–10 min$^{-1}$. The polymer preferably has a comonomer content, e.g., a vinyl acetate content of between 18 wt % to 30 wt % vinyl acetate in the copolymer. The balance of the copolymer typically comprises the ethylene monomer. An example of useful material typically is centered on an ethylene vinyl acetate polymer containing about 20±5 wt % vinyl acetate copolymer or an ethylene vinyl acetate material comprising about 27+5 wt % vinyl acetate comonomer. Other comonomers in the ethylene polymers preferably comprise methacrylate, vinyl acetate, N-butyl acrylate, other similar unsaturated monomers and mixtures of monomers thereof can be used. The polymer material used in the invention can be derived from a single polymeric raw material or source material or can be a blend of two or more polymer materials or source materials obtained from raw material manufacturers. The weight ratio of a second polymeric material to the first polymeric material used in the preparation of the adhesives of the invention can range from about 0.01 to about 10 parts by weight of the second polymeric material per each part by weight of the first polymeric material. Such blends can comprise a blend of an EVA with an ethylene methacrylate copolymer or a blend of an ethylene methacrylate copolymer with an ethylene n-butylacrylate copolymer or any variation thereof.

The adhesive composition of the invention can comprises at least one homogeneous ethylene α-olefin polymer which contains ethylene and at least one $C_3$ to $C_{16}$ α-olefin. Such ethylene α-olefin polymers are selected based on homogeneity, density and molecular weight distribution ($M_w/M_n$). Useful ethylene α-olefin polymers are characterized as having a narrow molecular weight distribution, less than 4, preferably less than 3, more preferably from 1 to 3, even more preferably from 1.25 to 2.5. The polymers are typically homogenous and random copolymers. Any monomer is randomly distributed within a given molecule and substantially all of the polymer molecules have the same ethylene/comonomer content. The homogeneous ethylene/α-olefin polymer comprises ethylene and at least one α-olefin monomer selected from the group consisting of an α-olefin, non-conjugated diene, and a cycloalkene such as propylene, isobutylene, 1-butene, 1-hexene, 4-methyl-1-pentene, 1-heptene, and 1-octene, cyclopentene, cyclohexene and cyclooctene, 1,4-hexadiene; 1,5-heptadiene; 4-vinyl cyclohexene; 1-allyl-4-isopropylidene cyclohexane; 3-allyl cyclopentene; 4-allyl cyclohexene; and 1-isopropenyl-4-butenylcyclohexene; dicyclopentadiene; alkenyl, alkylidene, cycloalkenyl, and cycloalkylidene norbornenes, such as 5-methylene-2-norbornene; 5-methylene-6-methyl-2-norbornene; 5-methylene-6,6-dimethyl-2-norbornene; 5-propenyl-2-norbornene; 5-(3-cyclopentenyl)-2- norbornene; 5-ethylidene-2-norbornene; 5-cyclohexylidene-2-norbornene; piperylene.

The molecular weight of the useful olefin polymer will be selected on the basis of the desired performance attributes of the adhesive formulation and can have a number average molecular weight of at least 800 grams/mole, preferably at least 1,300 and no more than 100,000 grams/mole. Ultra low molecular weight homogeneous ethylene α-olefin polymer are considered to have a number average molecular weight of less than about 11,000 g/mole. For adhesive applications, the homogeneous ethylene/α-olefin polymer typically has a melt index greater than about 800 g/10 min., more typically greater than about 900 g/10 min., preferably greater than about 950 g/10 min. The melt index inversely relates to the molten viscosity. The density of the ethylene α-olefin polymer will be selected on the basis of the desired performance attributes of the adhesive formulation. Typically however, the homogeneous ethylene/α-olefin polymer will have a density of at least 0.850 g/cm$^3$, preferably at least 0.860 to 0.900 g/cm$^3$, and more preferably about 0.860 0.890 g/cm$^3$.

The homogeneous ethylene α-olefin polymer will typically be present in the adhesive of the invention in an amount greater than about 40 wt-%, preferably greater than about 50 wt-%, and more preferably greater than about 60 wt-%. When employing two or more homogeneous ethylene α-olefin polymer, the first and second polymer will differ from each other with respect to the type of monomer or the molecular weight or melt index, or the density, or the molecular weight distribution. Accordingly, the first and second polymer may differ in number average molecular weight by at least 5000, preferably at least 10,000, and more preferably at least 20,000. In addition or in the alternative, the first and second polymers may differ in density by at least 0.005 g/cm$^3$, preferably by at least 0.01 g/cm$^3$.

The adhesive can use about 0.1 to 10 wt. % of a block polymer to increase cohesive strength in the adhesive and increase peal strength after application. Block polymers useful include ABA structures, AB structures, (A-B)$_n$ radial polymers, as well as branched and grafted materials. The B block is typically isoprene, butadiene, hydrogenated butadiene, hydrogenated isoprene, etc. Commercial embodiments include the Kraton® block polymer materials, (Shell Chemical Company, Houston, Tex.), Septon® (SEEPS) materials for Kuraray Co., Ltd., Europrene® block polymer materials, Sol T polymer materials (EniChem, Houston, Tex.), Vector® block polymer materials (Exxon/Dexco, Houston, Tex.). The A block (styrene or vinyl) content of the polymer ranges from 0.1 wt-% to about 50 wt-%. Typically, the aromatic A block concentration ranges from about 5 wt-% to about 45 wt-% based on the polymer. The styrene content can be less than about 25 wt-%, more preferably less than about 20 wt-% and most preferably from about 5 wt-% to about 15 wt-% styrene with respect to the total weight of the block copolymer for certain formulations. When employed with a ethylene/α-olefin polymer having a relatively high melt index, preferably the block copolymer comprises a hydrogenated block copolymer. For this embodiment the block copolymer contributes significantly to the cohesive strength of the adhesive composition. The molecular weight of a block copolymer relates to its solution viscosity at 25° C., for a given weight of polymer in (toluene) solvent. The amount of block copolymer employed for determining the solution viscosity depends on the molecular weight. For the higher molecular weight block copolymers, the solution viscosity is typically expressed as a function of a 10 wt-% or 15 wt-% block copolymer solution, whereas for more conventional and lower molecular weight block copolymers, a 25 wt-% block copolymer solution is employed. For 10 wt-% or 15 wt-%, the solution viscosity of the block copolymer for use in the invention ranges from about 100 cP to about 3103 cP at about 25° C. For a 25 wt-% block copolymer solution, the solution viscosity may range from about $10^2$ to about $10^5$ cP, preferably from about 100 to about 8·$10^4$ cP, more preferably from about 200 to about 3·$10^4$ and most preferably from about 200 to about 2·$10^5$ cP. For low viscosity adhesive compositions, preferably the solution viscosity of the block copolymer employed is less than 10·$10^3$ cP, more preferably less than about 5·$10^3$, even more preferably less than about 2.5·$10^3$ cP and most preferably less than about 2·$10^3$ cP. The block polymer is substantially hydrogenated in which the midblock is typically ethylene/butylene, ethylene/propylene, or mixtures thereof. Preferred block copolymers comprise substantially saturated materials having styrene endblocks and ethylene/butylene or ethylene/propylene midblocks and having a di-block content of less than about 70%, a di-block content of preferably less than about 50% and more preferably less than about 30%. The block copolymers useful herein preferably have a melt index of greater than about 20 grams/10 minutes, more preferably greater than about 30 g/10 min, even more preferably greater than about 50 g/10 min. and most preferably greater than about 60 g/10 min. The styrene content is preferably from about 10% to about 40% by weight of the block copolymer, more preferably from about 10% to about 35% by weight and most preferably from about 10% to about 30% by weight of the block copolymer. Other preferred Styrene-ethylene/propylene-styrene (hereinafter SEEPS) block copolymers are available from Kuraray Company, Ltd in Tokyo, Japan under the tradename of Septon®. and may also be utilized providing the block copolymer meets the diblock requirement. These block copolymers are useful from about 5 wt-% to about 30 wt-% of the adhesive. Kraton® G-1650, a linear styrene-ethylene/butylene-styrene block copolymer having a diblock content of 0%, an M.sub.N of about 113,000 and a styrene content of about 28%; and Septon® 4033 supplied by Kuraray, Japan, a linear styrene-ethylene/propylene-styrene block copolymer having a diblock content of 0%, an M$_n$ of about 108,000 and a styrene content of about 30% by weight of the copolymer. The midblocks are preferably ethylene/butylene, ethylene/propylene or isoprene and are more preferably ethylene/butylene or ethylene/propylene. The styrene content is preferably between about 10% and about 40% by weight of the block copolymer, more preferably from about 10% to about 35% by weight, even more preferably from about 10% to about 30% by weight and most preferably from about 10% to about 25% by weight. The melt index of these block copolymers is preferably greater than about 5 g/10 min. and more preferably greater than about 10 g/10 min. Useful examples include Kraton® 1652 available from Shell Chemical Co., a 100% linear SEBS block copolymer having about 29% styrene and a melt index of about 10 g/10 min. These block copolymers are useful from about 5 wt-% to about 50 wt-% of the adhesive, preferably from about 10 wt-% to about 50 wt-% of the adhesive and more preferably from about 10 wt-% to about 40 wt-% of the adhesive.

The composition of the present invention is preferably made by first preparing the thermoplastic component by melting and blending all the thermoplastic ingredients. The thermoplastic composition may be pelletized, pillowed, or cast into molds or drums, etc., for subsequent remelting and application. Alternatively, all the ingredients may be fed simultaneously at the appropriate rates into an extruder. The preferred tackifying resins for use in the adhesives of this invention have a softening point that is greater than about 120° C., preferably greater than 125° C., wherein the typical and most useful materials have a softening point that ranges from about 127° to about 145° C. A preferred class of tackifying resins include the petroleum hydrocarbon resins that are very light in color, aromatic modified, cycloaliphatic hydrocarbon resins. These materials are often hydrogenated to improve thermal stability and are typically made by first polymerizing aliphatic materials into an amorphous polymer composition which can then be post modified with aromatic components, hydrogenation, etc. to form a high melting tackifying material that is particularly effective in the adhesive materials of the invention. The polymer or polymer blends of the invention are combined with tackifying agent in an amount that ranges from about 30 to 80 wt % of the tackifying resin, often 45 to 75 wt % of the tackifying resin and in many embodiments of the invention about 50 to 65 wt % of the tackifying resin. In such compositions, the EVA polymer is typically present in an amount of greater than about 40 wt % of the polymer or polymer blend. Typically, in the adhesives of this invention, the weight ratio of the polymer or polymer blend to the tackifying resin is greater than about 1:1 and the adhesive softening point is typically in a range of about 70 to 82° C. (about 160 to about 180° F.) or about 74 to 77° C. (about 165 to 170° F.). The polymer or polymer blend is often used in embodiments of the invention in an amount of about 42 to 70 wt % and in a typical diaper or feminine disposable, it is used often in amounts that range from about 45 to about 65 wt % of the adhesive material.

The composition of the present invention may be applied by any hot melt application technique such as slot coating, spiral spraying, screen printing, foaming, engraved roller or melt blown adhesive application techniques. When applied in this manner, the inventive thermoplastic composition may be present as a coating, fiber, non-woven web, or film layer on at least one substrate or as a portion of an article. In one embodiment of the disposable article of the invention, typically at a minimum, comprises at least one film combined with a non-woven or woven fabric having a bonding layer of the adhesive of the material. The bonding layer can typically comprise a uniform layer, a spiral spray or a sprayed on or a fine line application of adhesive composition. The amount of adhesive combined with the film and the fabric comprises about 1 to 3 milligrams/lineal inch for Fineline applications and 1 to 8 milligrams/square inch for spiral spray applications. The adhesive typically is combined with the film or fabric by delivering the materials at an adhesive melt application temperature to effectively bond the film to fabric.

Ethylene Vinyl Acetate Copolymer
The preferred EVA is a high flow, 18–25 wt % vinyl acetate copolymer.
TYPICAL PROPERTIES

|  | Units (S1) | Typical Value[1] |
|---|---|---|
| Resin Properties |  |  |
| Vinyl Acetate | wt % | 18–25 |
| Melt Viscosity 190° C. | cP (mPa · sec) | 3200 (3200) |
| Wax Blend Viscosity[2] 121° C. | cP (mPa · sec) | 150 (150) |
| Density | g/cm³ | 0.947 |
| Bulk Density ASTM D-1895 (B) | lb/ft³ (kg/m³) | 33 (530) |
| Peak Melting Temperature | ° F. (° C.) | 162 (72) |
| Physical Properties |  |  |
| Softening Point, R & B | (° C.) | 80–85 |
| Tensile Strength[4] @ Break ASTM D-638 | psi (MPa) | 330 (2.3) |
| Elongation[4] @ Break ASTM D-638 | % | 95 |

-continued

Ethylene Vinyl Acetate Copolymer
The preferred EVA is a high flow, 18–25 wt % vinyl acetate copolymer.
TYPICAL PROPERTIES

|  | Units (S1) | Typical Value[1] |
|---|---|---|
| Hardness, 15s Shore A ASTM D-62240 | — | 79 |

[1]Values are typical and should not be interpreted as specifications.
[2]30% MV 02520, 70% 158° F. (70° C.) melting point paraffin wax.
[3]Physical properties were determined on compression molded specimens.
[4]Tensile testing was performed on Type IV specimens.

Ethylene Vinyl Acetate Copolymer
Another preferred EVA is a 27.5 wt % vinyl acetate copolymer.
TYPICAL PROPERTIES

|  | Units (S1) | Typical Value[1] |
|---|---|---|
| Resin Properties |  |  |
| Vinyl Acetate | wt % | 25–32 |
| Melt Viscosity 190° C. | cP (mPa · sec) | 3100 (3100) |
| Wax Blend Viscosity[2] 121° C. | cP (mPa · sec) | 150 (150) |
| Density | g/cm³ | 0.937 |
| Bulk Density ASTM D-1895 (B) | lb/ft³ (kg/m³) | 28 (449) |
| Peak Melting Temperature | ° F. (° C.) | 144 (62) |
| Refractive Index | — | 1.483 |
| Physical Properties |  |  |
| Softening Point, R & B | ° F. (° C.) | 169 (76) |
| Flexural Modulus, 1% secant ASTM D-790 | psi (MPa) | 640 (4.4) |
| Tensile Strength[4] @ Break ASTM D-638 | psi (kPa) | 142 (980) |
| Elongation[4] @ Break ASTM D-638 | % | 100 |
| Hardness, 15s Shore A ASTM D-2240 | — | 48 |

[1]Values are typical and should not be interpreted as specifications.
[2]30% MV 02528, 70% 158° F. (70° C.) melting point paraffin wax.
[3]Physical properties were determined on compression molded specimens.
[4]Tensile testing was performed on Type IV specimens.

Preferred Escorez 5600 Series
Petroleum Hydrocarbon Resins
ESCOREZ 5600 Series Resins are very light color aromatic modified, cycloaliphatic hydrocarbon resins.
PRODUCT SPECIFICATIONS

| Grades | 5600 | 5615 | 5637 | 5690 |
|---|---|---|---|---|
| Softening Point, R & B, ° C. | 100 to 106 | 115 to 121 | 127 to 133 | 87 to 93 |
| Color |  |  |  |  |
| YI, Initial Color[1] | 6 max. | 7 max. | 7 max. | 7 max. |
| YI, Aged 5 hours at 175° C.[1] | 75 max. | 75 max. | 61 max. | 77 max. |
| Aromaticity, % | 8 to 11 | 8 to 11 | — | 9.5 to 12 |
| Appearance | Clear, Free of Foreign Matter | | | |
| Melt Viscosity (Brookfield) |  |  |  |  |
| Test Temperature, ° C. | 140 | 160 | 180 | 130 |
| cP | 4300 | 3000 | 1800 | 3000 |

-continued

Preferred Escorez 5600 Series
Petroleum Hydrocarbon Resins
ESCOREZ 5600 Series Resins are very light color aromatic modified,
cycloaliphatic hydrocarbon resins.
PRODUCT SPECIFICATIONS

| Grades | 5600 | 5615 | 5637 | 5690 |
|---|---|---|---|---|
| Molecular Weight | | | | |
| Mw | 520 | 560 | 500 | 480 |
| Mn | 270 | 310 | 300 | 250 |
| Mz | 950 | 1000 | 910 | 900 |
| Tg, ° C. | 48 | 65 | 80 | 45 |
| Specific Gravity, 10/20° C. (IPOH) | 1.1 | 1.1 | 1.1 | 1.1 |
| Ash Content, wt % | <0.1 | <0.1 | <0.1 | <0.1 |
| Acid Number, mg KOH/g | <1 | <1 | <1 | <1 |

[1] Solution color as determined by measurement of a 50% (by weight) product in Toluene mixture.
[2] ExxonMobil Test Methods, some of which were developed from ASTM test methods, are available upon request.

EASTOTAC Resin H-142R
Product Data Sheet

| Property | Test Method | Typical Value, Units |
|---|---|---|
| Ring and Ball Softening Point | | 142° C. |
| Color, Gardner | | |
| Molten in 50 % Toluene | D6166 | 4 1.5 |
| Yellowness Index in 50% Toluene | E313 | 11 |
| Density | | 1.04 g/mL |
| Viscosity, Brookfield @ 190° C. | | 3000 cP |
| Form | | Flake |
| Acid Number | | <0.1 |
| Bulk Density | | 1.04 g/mL |
| Bromine Number | | 5 |
| Flash Point Cleveland Open Cup | | 321° C. (610° F.) |

DETAILED DISCUSSION OF THE INVENTION

The articles of the invention at a minimum comprise a film layer or a permeable layer adhesively joined with a substrate. The permeable layer can comprise a cellulosic tissue, a woven or non-woven fabric or other thin, flexible, porous or wettable sheet-like material. The tissue layer is a well known, typically loosely formed cellulosic sheet of high porosity or permeability. The fabric layer consists of a fluid permeable flexible material that can be made of either hydrophilic or hydrophobic fiber components. Woven and non-woven webs comprising the fabric can comprise natural or synthetic fibers or mixtures thereof. Woven and non-woven materials are well known and their construction methods have been practiced for many years. Woven fabrics are typically manufactured in weaving machines forming an interlocking mesh of fibers forming the layer. Non-woven fabrics can be made through a dry-laid or wet-laid method in carding processes, air laying processes or spun bond processes to produce a web that is mechanically, chemically or thermally formed. The fabric layers for use in the compounds and articles of this invention typically have a basis weight in the range of about 10 to 25, preferably 14 to 18 grams per square yard, a minimum dry tensile strength of at least 800 grams per $cm^2$ in the machine direction, and at least 200 grams per cm $^2$ in a cross machine direction. Synthetic materials commonly used in forming the fabric top sheets include rayon, polyester, polypropylene, polyethylene, nylon and others.

The substrate materials that can be used in the manufacture of the disposable articles of the invention, in combination with the tissue or woven or non-woven fabric, comprises any typical substrate used in the manufacture of disposable articles including, films, sheets, elastics, absorbents, cellulosic fluffs or fill, other tissue, woven or non-woven fabrics, etc.

Absorbent layers can be adhered to other substrates using the adhesives of the invention. Such absorbent layers can comprise cellulosic pulp or fluff. Such fluff layers are often formed and wrapped in tissue to provide mechanical integrity to the fluff which has little inherent integrity. Fluff is typically manufactured through formation of cellulosic fibers. However, other materials can be utilized to form high absorbent fluff or pulp layers.

Elastic bands or elements can be used in the manufacture of the disposable articles of this invention.

The film or sheet-like layer used in the invention comprises a flexible sheet-like or film substrate. Such films are typically manufactured from thermoplastic resins and take the form of a thin layer having a thickness of about 0.5 to 2.0 mils. Such films comprise polyethylene, polypropylene, ethylene-propylene copolymers, ethylene acrylate copolymers, ethylene vinyl acetate copolymers, polyvinyl chloride polymers, polyvinylidene chloride polymers, polyester polymers and others. Such films can be perforate or imperforate. In addition to the above materials used in the composite articles of the invention, a variety of other materials can be used, including other wrapping materials, deodorants, perfumes, dyes, and decorative appliqués, which provide further absorbency, instructional legends, and pleasing appearance or smells.

In somewhat greater detail, the adhesives of the invention can be used in the manufacture of disposable articles including disposable diapers, incontinent devices or diapers, feminine pads, and disposable bed pads by adhering a porous layer to a substrate. The assembly operations that deserve note include adhering a porous non-woven layer to a back sheet and adhering a tissue layer to an absorbent core.

In the manufacture of absorbents for disposables, it is common to wrap loosely assembled fluff or batts of absorbent material within a tissue overwrap. In such manufacture, the tissue surrounds the absorbent material in an overlapping fashion such that the spray-on adhesive can be applied to the overlap area, causing the adhesive to penetrate the overlap to contact the underlying fluff or batt. The spray-on adhesive in contact with the tissue and absorbent material forms a strong mechanical bond which maintains the tissue wrap and provides mechanical support and integrity to the underlying fluff or absorbent batt material. As a result of using the manufacturing techniques of the invention, the tissue-covered absorbent material obtains substantial mechanical integrity from the adhesive and tissue structure. During use, the tissue and adhesive maintains the fluff or batt in place and prevents movement of the absorbent material resulting in an inappropriate segregation of absorbent material in a small portion of the absorbent article. Such mechanical integrity insures that the absorbent material stays in place to provide absorbency and protection.

In the manufacture of composite articles, the fluid permeable fabric top sheet is adhered to a film back sheet. An absorbent layer can be introduced into the space between the fabric layer and the back sheet. Typically a fluid in contact with the fabric layer passes through the fabric layer and is absorbed and held within the absorbent layer. The absorbent core typically comprises a highly porous, highly absorbent loosely contacted fluff, wrapped or encased within a tissue cover. The absorbent fluff typically has little mechanical integrity. The tissue wrap or cover, once adhered to the fluff, provides the absorbent layer with substantial dimensional integrity preventing the absorbent material from migrating or collecting in an inappropriate portion of the diaper. The tissue wrap ensures that the absorbent material remains evenly distributed within the envelope created by the back sheet and the fabric layer. The manufactured diaper or the components of the diaper can have elastic bands or segments adhesively attached to provide security for the wearer. such elastic bands create a snug fit at the waist and the leg apertures of the disposable articles. The adhesive compositions of the invention can be used to form bonds between the surfaces of the film materials between apertured films and non-apertured films, between tissue and non-woven or woven fabric layers, between absorbent fluff and tissue overwraps, and between elastic bands or elements and any structural component of the disposable diaper.

In construction methods for the preparation of the disposable articles of the invention, the adhesives are typically applied from spray heads that deliver the adhesive at elevated temperatures (typically above about 250° F. and typically in the range of 275–400° F.). The spray heads have apertures that range from about 0.01 to about 0.04 inch. Under the operating conditions of typical adhesive spray machines, the diameter of the sprayed adhesive fiber can range from the size of the aperture to as little as about 0.001 inches depending on operating conditions. Depending on the end use and final bond strength desired, the adhesive can be used at application amounts that range from 0.5 milligrams per square inch to as much as 10 milligrams per square inch. preferably, because of the unique properties of the adhesives of this invention, the adhesives can be used at an application amount of from about 0.5 milligrams per square inch to 5 milligrams per square inch. Most preferably, in disposable diaper construction the adhesive of the invention is used at an application rate of about 1 to about 4 milligrams per square inch.

During the manufacture of disposable articles using the adhesives of the invention, two modes of application are preferred. One mode of operation involves spraying the adhesive upon a fabric, such as a tissue, a woven or non-woven web, or other material having permeability to the adhesive. Such sprayed-on adhesive can penetrate the permeable tissue, non-woven or woven fiber, to cause the sheet to be embedded in the adhesive and adhered to the substrate such as an absorbent layer, back layer, or film. Alternatively, the adhesives of the invention can be directly applied to back sheet or film and the tissue, woven or non-woven fabric, or other material can be applied to the adhesive on the film. The adhesive retains sufficient liquidity that it can penetrate pores or apertures in the fabric to form a mechanical bond. In the manufacture of tissue fluff absorbent cores, the fluff is typically wrapped by tissue, the tissue layer can be wrapped around the fluff and can overlap. Adhesive can then be sprayed on the overlapping portion of tissue outerwrap, can penetrate the wrappings and adhere the tissue to the fluff ensuring that the fluff obtains dimensional stability from adherence to the outer wrap.

In somewhat greater detail, the sprayable, hot melt adhesive compositions of the invention typically comprise an effective amount of a base and an effective amount of a tackifying agent to form an effective adhesive that has the unique property that after spraying and cooling retains sufficient liquidity to penetrate a porous layer.

TABLE 1

EVA Based Adhesive

| EVA | >40 | 42–80 | 45–75 |
|---|---|---|---|
| Second EVA | 0–40 | 10–30 | 15–25 |
| Tackifier | 30–80 | 45–75 | 50–65 |
| Wax | 0–5 | 0–5 | 0–5 |
| STAB | 0–0.2 | 0.01–0.2 | 0.01–0.2 |

TABLE 2

EAO Based Adhesive

| EAO | 35–85 | 30–80 | 50–75 |
|---|---|---|---|
| Second Polymer | 0–40 | 10–30 | 15–25 |
| Tackifier | 30–80 | 45–75 | 50–65 |
| Wax | 0–5 | 0–5 | 0–5 |
| STAB | 0–0.2 | 0.01–0.2 | 0.01–0.2 |

TABLE 3

EAO/ABA Based Adhesive

| EPO | 35–85 | 40–80 | 45–75 |
|---|---|---|---|
| ABA | 0.1–10 | 0.2–8 | 0.3–6 |
| Tackifier | 30–80 | 45–75 | 50–65 |
| Wax | 0–5 | 0–5 | 0–5 |
| STAB | 0–0.2 | 0.01–0.2 | 0.01–0.2 |

The hot melt adhesives of the invention are made in common hot melt manufacturing equipment. In the manufacture of the hot melt adhesives of the invention, the EVA copolymers typically added to a melt comprising either the tackifier or the plasticizer material or mixtures thereof. Such additions facilitate the blending of the EVA copolymer into a smooth, uniform mixture. In such a manufacturing regimen, either the tackifier or the plasticizer or a portion thereof is added to the manufacturing equipment under inert atmosphere and is heated and agitated until melted. The EVA copolymer is then added to the melt at a rate such that the mixture forms a uniform smooth blend within a reasonable period. Antioxidant materials used in the manufacture of the adhesive can be added to the melt prior to, with, or after the addition of the block copolymer. Once a smooth blend of the copolymer in conjunction with an adhesive component is formed, the balance of the components of the hot melt adhesives can be added at a convenient rate. Once the uniform blend of all the adhesive ingredients is formed, the adhesive can be drawn off and packaged in a convenient form including in drums, blocks, pillows, pellets, granules, etc.

The following examples provide additional information with respect to the manufacture of the adhesives of the invention and include the best mode. Following the standard laboratory blending procedures the following compositions were blended into a hot melt adhesive:

EXAMPLES 1–13

The table below is a summary of data generated for these products. About 2000 g batches of each were made by melt blending in a lightning mixer at 300° F. The Brookfield Thermosel viscosity and Mettler Softening Point were measured. We laminated polyethylene and non-woven films using a Nordson spiral spray head. We used both spiral spray and Fineline patterns. The non-woven/polyethylene laminate was tested for initial T-peel adhesion.

The best products have a maximum initial spiral spray value with minimal falloff of aged spiral spray values. The best products appear to be those with 25–30% tackifying resin and EVA primarily composed of 20% vinyl acetate. Products that are made completely from 28% vinyl acetate EVA tend to be soft and can have cohesive problems. The lower vinyl acetate EVA is more crystalline and cohesive.

|  | Spiral peel | | Fineline peel | | Viscosity @ | Softening |
|---|---|---|---|---|---|---|
| Example Nbr. | Escorez 5637 | EVA 28/2500 | EVA 20/2500 | Initial (g) | Aged (g) | Initial (g) | Aged (g) | 149° C. 300° F. | Point (° F.) |
| 1 | 0.15 | 0.425 | 0.425 | 11 | 85 | 56 | 53 | 7250 | 174 |
| 2 | 0.2 | 0.6125 | 0.1875 | 70 | 107 | 67 | 118 | 6465 | 169 |
| 3 | 0.25 | 0.75 | 0 | 102 | 180 | 44 | 68 | 6125 | 165 |
| 4 | 0.35 | 0 | 0.65 | 107 | 121 | 21 | 38 | 4410 | 174 |
| 5 | 0.25 | 0.1875 | 0.5625 | 57 | 170 | 60 | 82 | 5410 | 171 |
| 6 | 0.3 | 0.5125 | 0.1875 | 125 | 127 | 37 | 52 | 5300 | 166 |
| 7 | 0.35 | 0.325 | 0.325 | 117 | 148 | 49 | 71 | 4444 | 169 |
| 8 | 0.15 | 0 | 0.85 | 28 | 117 | 88 | 60 | 6750 | 176 |
| 9 | 0.15 | 0.85 | 0 | 67 | 73 | 59 | 34 | 7000 | 167 |
| 10 | 0.15 | 0 | 0.85 | 28 | 54 | 104 | 63 | 6680 | 177 |
| 11 | 0.35 | 0.65 | 0 | 49 | 345 | 45 | 46 | 4310 | 170 |
| 12 | 0.35 | 0 | 0.65 | 92 | 93 | 17 | 27 | 4680 | 174 |
| 13 | 0.31 | 0.35 | 0.34 | 78 | 188 | 60 | 83 | 4750 | 170 |

EXAMPLES 14–19

The table below is a summary of data generated for the ethylene olefin products. About 2000 g batches of each were made by melt blending in a lightning mixer at 300° F. The Brookfield Thermosel viscosity and Mettler Softening Point were measured. We laminated polyethylene and non-woven films using a Nordson spiral spray head. We used both spiral spray and Fineline patterns. The non-woven/polyethylene laminate was tested for initial T-peel adhesion 120° F.

|  | Example 14 | Example 15 | Example 16 | Example 17 | Example 18 | Example 19 |
|---|---|---|---|---|---|---|
| Ethylene/ octene polymer |  |  | 70.0 | 65.0 | 65.0 | 60.0 |
| EVA 28% EVA-2500 MI | 69.8 |  |  |  |  |  |
| ABA[1] |  |  |  |  | 5.0 |  |
| ABA[2] |  |  |  |  |  | 5.0 |
| EVA 20% EVA-2500 MI |  | 69.8 |  |  |  |  |
| Eastotac 142 tackifier | 30.0 | 30.0 |  |  |  |  |
| Escorez 5637 tackifier |  |  | 29.8 | 34.8 | 29.8 | 34.8 |
| Irganox 1010 antioxidant | 0.2 | 0.2 | 0.2 | 0.2 | 0.2 | 0.2 |
| Spiral Peel (Initial) Adhesion | 93 | 38 | 111 | 143 |  |  |
| Fineline Peel (Initial) Adhesion | 89 | 35 | 72 | 96 |  |  |
| Viscosity @ 300° F. | 5380 | 5210 | 8480 | 7600 |  |  |
| Mettler Softening Point | 170 | 175 | 172 | 174 |  |  |

The ethylene/octene polymer is a 1000 MI ethylene octene (density of about 0.860 to 0.890) polymer. The peel values of the Ex. 17 are equivalent to what are obtained from the best commercially available SBC (PSA) based products on the market. Similar quality was obtained in Exs. 14 and 16. Examples 17 and 18 are prepared in 2000 g batches by melt blending in a lightning mixer at 300° F. ABA[1] is a SEPS Kraton G1652, ABA[2] is a SEEPS Septon 4033.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A hot melt adhesive composition comprising:
    (a) greater than about 40 wt % of an ethylene $C_3$ to $C_{18}$ α-olefin polymer composition comprising about 8 to 14 wt. % α-olefin having a melt index greater than 800 gm–10 $min^{-1}$; and
    (b) about 20 to 40 wt % of a hydrogenated hydrocarbon tackifying resin with a softening point greater than 125° C.;
    wherein the weight ratio of the polymer composition to the resin is greater than about 1:1.

2. The composition of claim 1, wherein the adhesive additionally comprises about 0.1 to 10 wt.-% of a block polymer and has a softening point of less than about 95° C.

3. The composition of claim 1, wherein the polymer composition has a melt index greater then 9.950 gm–10 $min^{-1}$ and the adhesive has a softening point of less than about 85° C.

4. The composition of claim 1, wherein the weight ratio is greater than 1.5:1.

5. The composition of claim 1, wherein the weight ratio is greater than 1.8:1.

6. The composition of claim 1, wherein the tackifying resin has a softening point of about 127 to 145° C.

7. The adhesive of claim 1, wherein polymer comprises is present in; the adhesive at a weight ratio of polymer:resin of at least 2:1.

8. The adhesive of claim 1, wherein the ethylene/α-olefin polymer is present in an amount of at least about 60 wt-%.

9. The adhesive of claim 8, wherein the ethylene/α-olefin polymer has a melt index greater than 950 gm–10 min$^{-1}$.

10. The adhesive of claim 8, wherein the resin is present in the adhesive in an amount of 20 to 40 wt %.

11. The adhesive of claim 1, wherein the ethylene/α-olefin polymer comprises a blend of a first ethylene/α-olefin polymer and a second ethylene/α-olefin polymer wherein the first has MI difference than the second.

12. The adhesive of claim 1, wherein the adhesive consists essentially of greater than 40 wt % of ethylene/octene polymer composition comprising about 8 to 14 wt. % octane, the polymer having a melt index of about 850 to 1250 gm–10 min$^{-1}$ and about 30 to 40 wt % of a hydrogenated hydrocarbon tackifying resin with a softening point greater than about 125° C.; wherein the weight ratio of the polymer to the resin is greater than about 1:1.

13. The adhesive of claim 1 wherein the adhesive has a viscosity of 2000 cPs to $10^5$ cPs at 150° C. the adhesive has a softening point of less than about 85° C.

14. The adhesive of claim 1 wherein the adhesive has a viscosity of 4300 cPs to 7300 cPs at 150° C. and a and the adhesive has a softening point of less than about 95° C.

* * * * *

UNITED STATES PATENT AND TRADEMARK OFFICE
CERTIFICATE OF CORRECTION

PATENT NO. : 6,846,876 B1
DATED : January 25, 2005
INVENTOR(S) : Quinn

It is certified that error appears in the above-identified patent and that said Letters Patent is hereby corrected as shown below:

Column 15,
Lines 1-2, "wherein polymer comprises is present in; the adhesive" should read
-- wherein polymer is present in the adhesive --
Line 13, "difference than the second." should read -- different than the second. --

Signed and Sealed this

Twelfth Day of July, 2005

JON W. DUDAS
*Director of the United States Patent and Trademark Office*